(12) United States Patent
Sander

(10) Patent No.: US 7,480,093 B2
(45) Date of Patent: Jan. 20, 2009

(54) OPTICAL SYSTEM WITH DISPLAY

(75) Inventor: Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 246 days.

(21) Appl. No.: 11/279,405

(22) Filed: Apr. 12, 2006

(65) Prior Publication Data

US 2006/0250684 A1 Nov. 9, 2006

(30) Foreign Application Priority Data

Apr. 21, 2005 (DE) ................ 10 2005 018 432

(51) Int. Cl.
*G02B 21/36* (2006.01)
*G02B 21/00* (2006.01)

(52) U.S. Cl. ....................... 359/369; 359/368

(58) Field of Classification Search ......... 359/368–390, 359/800–819, 618–630
See application file for complete search history.

(56) References Cited

U.S. PATENT DOCUMENTS

| 5,134,662 | A | * | 7/1992 | Bacus et al. | ................. 382/133 |
| 5,420,716 | A | * | 5/1995 | Fukaya | ........................ 359/368 |
| 6,364,268 | B1 | * | 4/2002 | Metelski | ..................... 248/317 |
| 6,468,676 | B1 | * | 10/2002 | Ueda et al. | ................... 428/690 |
| 7,016,108 | B2 | * | 3/2006 | Kolb et al. | .................... 359/368 |
| 2003/0181803 | A1 | * | 9/2003 | Sander | ....................... 600/407 |
| 2004/0111183 | A1 | * | 6/2004 | Sutherland et al. | .......... 700/245 |
| 2004/0196548 | A1 | * | 10/2004 | Mannss et al. | .............. 359/368 |
| 2005/0041282 | A1 | * | 2/2005 | Rudolph et al. | ............. 359/368 |
| 2006/0274407 | A1 | * | 12/2006 | Fox et al. | ..................... 359/384 |

OTHER PUBLICATIONS

"Der Bildschirm auf Folie rückt näher", BMBF Pressemitteilung (Press Release), Aug. 31, 2003.
Schulze, Manfred, "Leuchtende Folien sollen bald LCDs verdrängen", Apr. 4, 2003, VDI nachrichten No. 14.
Schulz, Werner, "Spannende innovationsdynamik wie aus dem Lehrbuch", Apr. 4, 2003, VDI nachrichten No. 14, p. 27.
Schulz, Werner, "OLEDs—Besser klein als gar nicht", Apr. 4, 2003, VDI nachrichten No. 14, p. 28.
Hanke et al., "Leuchtendes Plastik—Stoff für Fernseher und Displays von morgen", Pro-physik, May 19, 2003.

* cited by examiner

*Primary Examiner*—Thong Nguyen
(74) *Attorney, Agent, or Firm*—Hodgson Russ LLP

(57) ABSTRACT

A surgical microscope system (1, 2, 3, 4, 5, 6) having a display (7a-7e). Data essential for the surgical procedure, for example video images, are displayed in the observer's immediate field of view, thus making it unnecessary to turn one's head away from the surgical visual field. Because of its optical properties, the display (7a-7e) can also be attached, for example, on the curved exterior of the microscope body (2) or also on an X-Y coupling (6) that may be present. An rigid OLED display or a flexible OLED display is preferably used.

7 Claims, 3 Drawing Sheets

OPTICAL SYSTEM WITH DISPLAY

CROSS REFERENCE TO RELATED APPLICATIONS

This application claims priority of the German patent application 10 2005 018 432.4 filed Apr. 21, 2005 which is incorporated by reference herein.

FIELD OF THE INVENTION

The invention relates to an optical system having one or more displays, in particular to a surgical microscope system.

BACKGROUND OF THE INVENTION

Technical data, for example the microscope's magnification, have heretofore been displayed mechanically or electrically on the microscope housing or on a display, in particular on a monitor. Video images have been presented via a monitor that was attached to the stand (see FIG. 1, existing art).

Such monitors are known, and so-called flat screens (e.g. TFT displays) are usually used today.

Surgical microscopes are indispensable in modern surgery. A magnification from 3× to 40× is selected as required. This allows surgeons to operate even on structures that are almost invisible to the naked eye, for example capillary blood vessels or nerves. Surgical microscopes also provide excellent illumination of the surgical field.

Surgical microscopes are used especially in neurosurgery, but also in other surgical specialties such as ear, nose and throat surgery, ophthalmology, and plastic and reconstructive surgery. Its light source is incorporated directly into the surgical microscope. The use of surgical microscopes makes it possible, for example in the case of microsurgical procedures on the brain or the spinal column, for incisions to be kept very small.

In the case of microsurgical procedures in particular, however, there are certain peculiarities as compared with procedures in which a surgical microscope is not used. For example, the surgeon and the surgical microscope must be located particularly close to the surgical field. The microscope body thus blocks the view of a surgical nurse, who can then observe the progress of the operation only on monitors in the operating room. Transfer devices on the surgical microscope serve this purpose. An anesthesiologist can also observe the progress of the operation via monitors in this fashion.

According to the presently existing art, however, a surgeon must also usually look at external monitors while working, in order to obtain additional information about the patient or about his equipment (e.g. phacoemulsifier, electrocautery, etc.). This requires turning one's head away from the microscope and toward the monitor, which is impractical and disadvantageous in terms of execution of the surgery.

Technical data of the surgical microscope and video images and external or internal data should therefore be shown to the surgeon at a point as close as possible to the surgical microscope, so that the surgeon does not need to look too far away from the surgical field. Data overlay systems that present their information directly in the microscope image have therefore been developed. This is achieved at present by means of a complex optical module in the interior of the microscope.

SUMMARY OF THE INVENTION

It is thus the object of the present invention to make available to users an optical system, in particular a surgical microscope system, that displays data to the operating surgeon without costly and complex optical modules and with the least possible interruption of or interference with the surgical procedure.

An improvement according to the present invention of this situation can be achieved, in a first step according to the present invention, in that the display is displaced from its previous attachment location on the stand or on a frame in the room, directly onto the microscope housing or at least into the immediate vicinity of the surgeon.

In a second step according to the present invention, a choice was made as to which presently known displays or display capabilities might best correspond to the desired attachment location. In this context, the display ideally should be relatively small so that there is room on the microscope body or on the X-Y coupling. An X-Y coupling is a displacement carriage for the X and Y axes located in the horizontal plane, which moves the entire microscope body and with which modern surgical microscope stands are usually equipped. The display should ideally also be capable of being attached to the curved outer surface of the microscope housing itself. It is furthermore necessary for the display to exhibit high luminosity, in order to eliminate unpleasant adaptation by the surgeon's eye from the bright surgical light to a low-luminosity display.

The inventor has recognized that so-called OLEDs are best suited for this. OLEDs are organic light-emitting diodes that are made up of self-luminous layers of plastic less than a thousandth of a millimeter thick. They are called "organic" because the long-chain polymer hydrocarbon compounds that constitute the basis for the plastics that are used are organic. Displays that are manufactured from such plastics require no background illumination, are very thin, and have far greater luminosity and wider viewing angles than conventional TFT displays or expensive liquid crystal displays (LCDs). To ensure that the polymers retain their luminosity for an effectively long time, they must not come into contact with oxygen from the air or water. They are therefore sealed with a thin piece of glass, although this makes the displays rigid again. In recent experiments, however, a flexible PET film is used for sealing against oxygen, thus creating flexible OLED displays that can also be manufactured in different formats. This makes it possible to equip variously shaped support surfaces, including curved ones, with such displays.

According to the present invention, these properties allow corresponding rigid and flexible OLED displays to be attached directly to the microscope housing or onto immediately adjacent microscope components. It is accordingly now possible to display, for example, video images, technical data such as the magnification coefficient, electronic unit menus, operational readiness, illumination status, and more, in the surgeon's immediate visual field.

In order to control the OLEDs and to select the displayed data, it is furthermore intended to be within the context of this invention to equip the OLEDs used therein with antimicrobial touch pads.

BRIEF DESCRIPTION OF THE DRAWINGS

The invention will be explained in more detail, in symbolic and exemplifying fashion, with reference to FIGS. 2 and 3. The Figures are described in continuous and overlapping fashion. Identical reference characters denote identical components; reference characters having different indices indicate functionally identical or similar components. In the drawings.

DETAILED DESCRIPTION OF THE INVENTION

Figure 1:
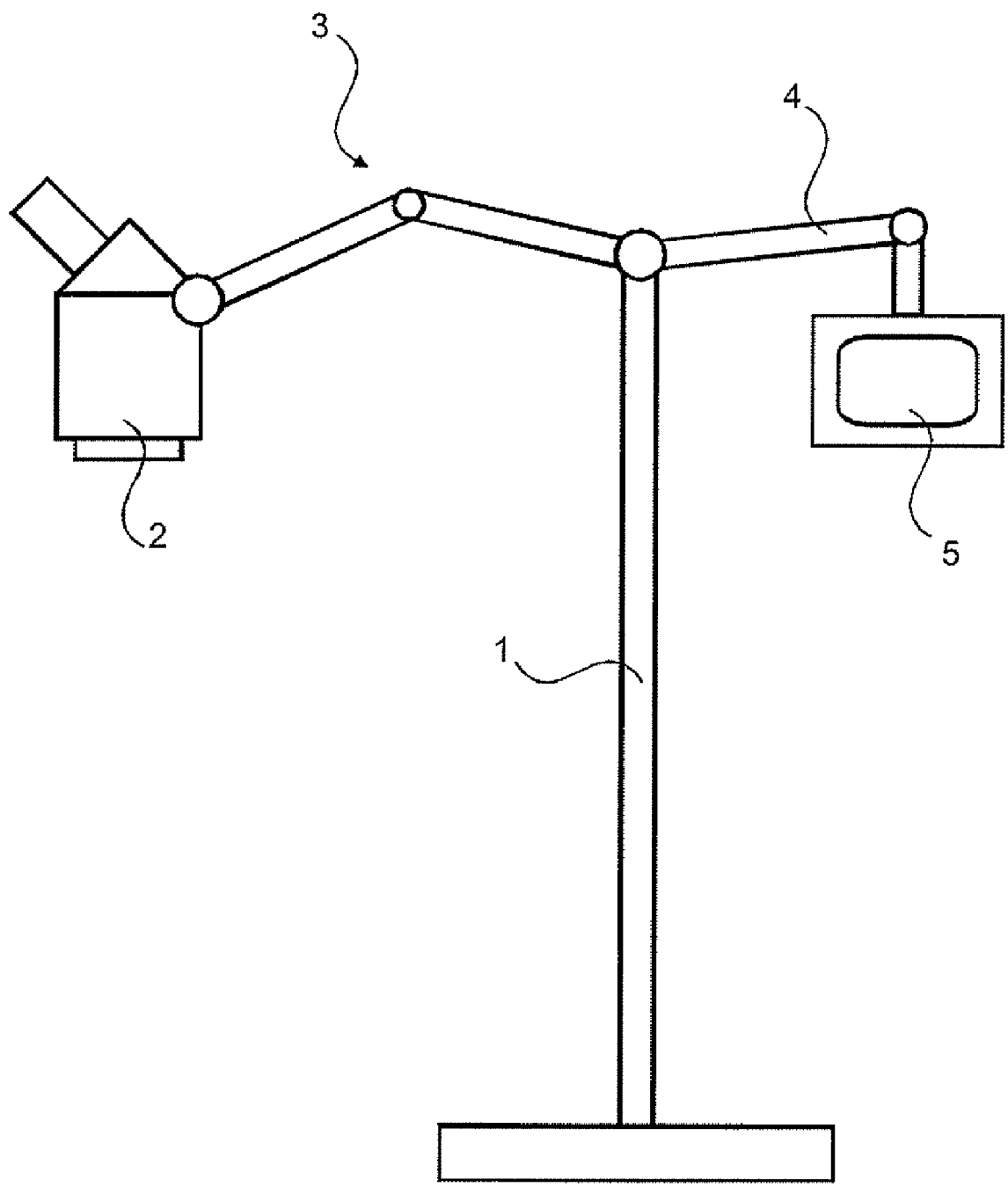
FIG. 1 shows the existing art in the form of a conventional surgical microscope having a stand and an externally arranged monitor.

FIG. 1 depicts a surgical microscope according to the existing art. Two carrier arms 3 and 4 are mounted on a stand 1. The one carrier arm 3 carries a microscope 2, and the other carrier arm 4 carries a monitor 5.

Figure 2:
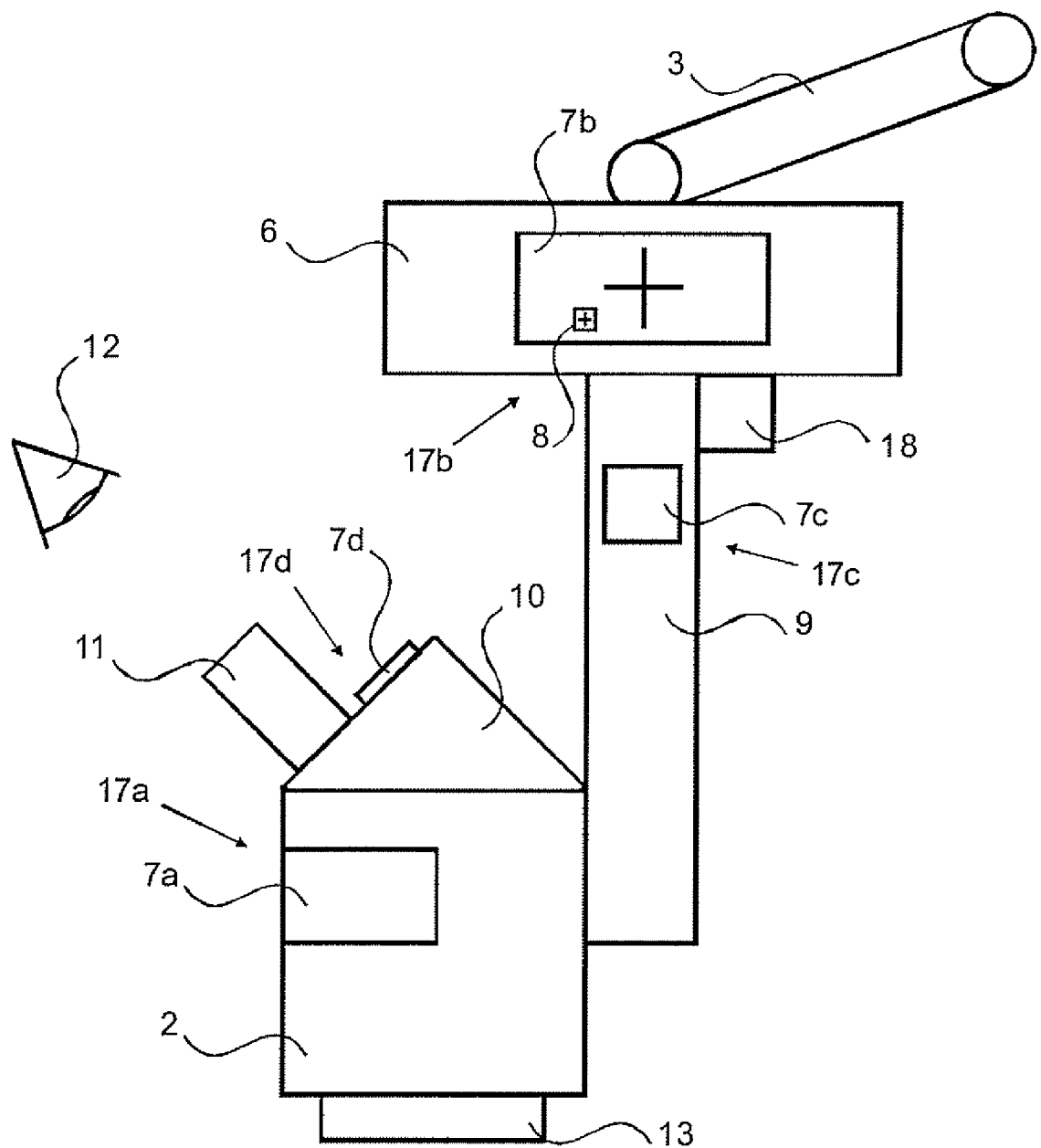
FIG. 2 shows the arrangement according to the present invention of an OLED display in the surgeon's immediate field of view, at four different possible attachment points.

FIG. 2 shows only the microscope-related portion of a conventional surgical microscope assemblage, specifically an X-Y coupling 6 and microscope body 2 that is secured pivotably on carrier arm 3. Microscope body 2 itself is carried by a microscope carrier arm 9. The microscope comprises a main objective 13, and an eyepiece tube 10 having eyepieces 11 (only one being visible because the two stereoscopic channels are located behind one another in this side view) into which a symbolic viewer's eye 12 looks. According to the present invention, an OLED display 7a or 7b can be arranged directly on microscope body 2 or on X-Y coupling 6. An OLED film that adapts itself to the usually round cross section of the microscope housing is particularly advantageous for arrangement on microscope body 2.

In addition, a surgical microscope according to the present invention can be equipped, for example, with a respective OLED display 7a or 7b both on microscope body 2 and also on X-Y coupling 6. Provision is made in this case, according to the present invention, for the presentations on the two OLED displays 7a and 7b both to be identical; but as another implementation, only microscope-specific data that are more useful to the surgeon are displayed on microscope display 7a, whereas data more relevant only to operating room personnel, or data that the surgeon requires only in specific situations, are displayed on X-Y coupling display 7b. The latter data include, in particular, information as to the point at which the microscope is currently positioned. For this, according to the present invention, the current position of the microscope within the entire possible field of movement of the microscope is indicated by means of a position symbol 8. The surgeon thus obtains, if need be, valuable information as to whether he or she can still reach a desired microscope position using the smaller but much more precise displacement mode via X-Y coupling 6, or whether he or she must resort to the substantial coarser pivoting of the entire carrier arm 3.

Provision is additionally made, according to the present invention, that an OLED display 7c, whether a rigid or a flexible one, can be arranged on microscope carrier arm 9, or that a further OLED display 7d can even be arranged on eyepiece tube 10. It is also within the scope of the invention to equip a surgical microscope stand with OLED displays at all four of the attachment locations disclosed, and to supply the four different OLED displays all with the same data or with different data.

Figure 3:
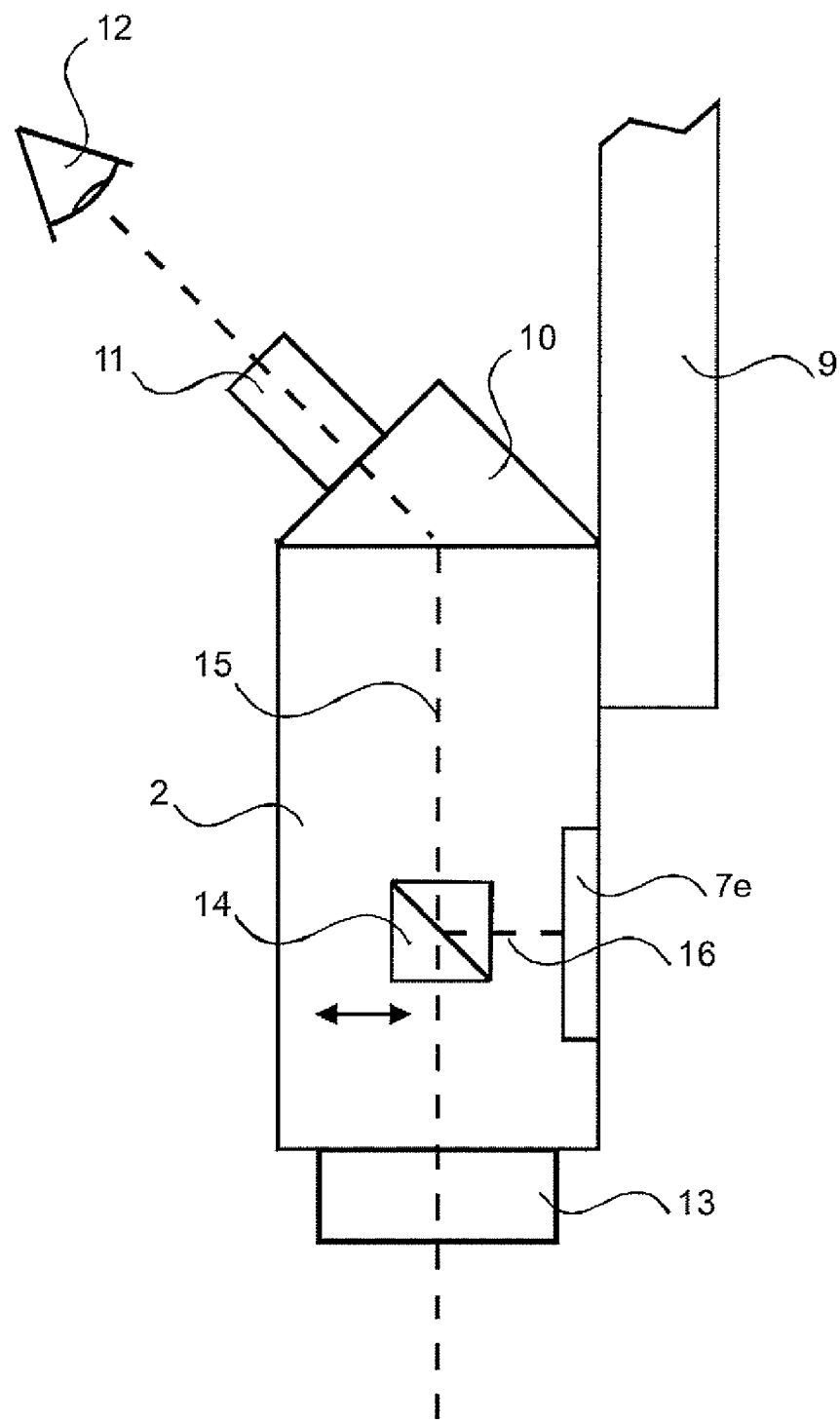
FIG. 3 shows an arrangement of a surgical microscope having an OLED display whose image is overlaid into at least one beam path.

FIG. 3 schematically shows the configuration of a surgical microscope according to the present invention in which an OLED display 7e is provided for overlay into one or both beam paths 15. A displaceable splitter prism 14 which optionally, as desired by the surgeon, couples the image of OLED 7e via an overlay beam path (depicted with its axis 16) into microscope beam path 15, can be provided for this purpose. Depictions of imaging optics have been omitted. According to a further variant embodiment of the present invention, OLED 7e can be configured in double-sided fashion. In other words, an OLED is used that has one display surface toward the inner side of the microscope. The image on this display surface is used for overlay into one or both beam paths of the microscope. In addition thereto, the same OLED also has a second display surface that faces outward. The display surfaces can present the same or different information.

The following existing art is relevant to flexible OLED displays (OLED films) and their applications:

The press release of the German Federal Ministry for Education and Research (BMBF Deutschland) entitled "Another step toward film-based display screens" [Der Bildschirm auf Folie rückt näher], dated Aug. 31, 2003 (Aktuell 154/03), reports on a research group at the Institute for Applied Light Physics [Institute für Angewandte Photophysik] of the Technical University of Dresden. This research group has developed low-molecular-weight organic light-emitting diodes (OLEDs) that supply the brightness necessary for display screen applications at a voltage of only 2.5 volts. Because the organic layers are very thin, these new OLEDs are suitable for constructing display screens even on flexible materials, for example on films. Self-luminous OLED-based display screens have several advantages over established liquid crystal displays (LCDs): they possess a wide viewing angle, display excellent moving images, and consume little energy. Further details may be found at the Web site http://www.b-mbf.de/press/924.php.

In Aachen/Chemnitz VDI (Society of German Engineers [Verein Deutscher Ingenieure]) Communications of Apr. 4, 2003 under the title "Luminous films may soon replace LCDs" [Leuchtende Folien sollen bald LCDs verdrängen], the author, Manfred Schulze, reports on research activities in the field of OLEDs, citing as the most important advantages the much higher luminosity, a wide viewing angle, low weight, and flexible display surfaces.

In Düsseldorf/Nice VDI Communications no. 14 of Apr. 4, 2003 under the title "Exciting innovation right from the textbook" [Spannende lnnovationsdynamik wie aus dem Lehrbuch], the author, Werner Schulz, reports on a variety of OLED types using a table that compares manufacturers and current maximum service lives. This article also explains the structural differences between LCDs and OLED displays and describes a few application examples, for example high-tech shavers or digital cameras.

In the same VDI Communications of Apr. 4, 2003, Werner Schulz reports, in a further article entitled "OLEDs—better small than not at all" [OLEDs—Besser klein als gar nicht], on OLEDs made by Universal Display Corporation (UDC) in Ewing, N.J., where full-color displays are being developed.

A further article appeared in Pro-physik on May 19, 2003 under the title "Luminous plastic—a material for tomorrow's TVs and displays" [Leuchtendes Plastik—Stoff für Fernseher und Displays von morgen], in which the authors, Benjamin Hanke and Till Mundzeck, report on further possible applications of OLEDs.

An article in "Wissenschaft aktuell (optics)" of Mar. 10, 2004, entitled "Double-sided LCD display screen: images on both sides" [Doppelseitiger LCD-Bildschirm: Bilder auf beiden Seiten], presented double-sided LCDs that use transparent circuit boards. It is obvious that with OLEDs' long-chain polymers that are transparent on both sides, OLED displays that emit from both sides can likewise be manufactured. A further variant configuration of the present invention (the embodiment of FIG. 3) therefore provides for a double-sided display, in particular an OLED display, to be arranged on the microscope housing in such a way that light from the inwardly-directed display surface is overlaid into one or both microscope beam paths by means of an optical imaging system. The other display, emitting light outward, provides further information for the surgeon or his or her auxiliary personnel.

PARTS LIST

1 Stand
2 Microscope body
3 Carrier arm for a microscope body 2
4 Carrier arm for a monitor 5
5 Monitor
6 X-Y coupling
7a-7e OLED (display)
8 Position symbol
9 Microscope carrier arm
10 Eyepiece tube
11 Eyepiece
12 Viewer's eye
13 Main objective
14 Splitter prism
15 Microscope beam path
16 Overlay beam path
17a-17d Attachment locations in surgeon's immediate field of view
18 Control system

What is claimed is:

1. A surgical microscope system comprising:
a stand having a carrier arm;
a microscope body having an eyepiece tube;
an X-Y coupling for mounting the microscope body on the carrier arm;
two displays arranged each at a different attachment location selected from a group of attachment locations consisting of: on an exterior of the microscope body, on the X-Y coupling, on the carrier arm, and on the eyepiece tube, each display being arranged in the immediate field of view of a viewer's eye; and
a control system operable to display identical data on both of the two displays or different data on the two displays.

2. The surgical microscope system according to claim 1, wherein at least one of the two displays is an organic light-emitting diode (OLED) display.

3. The surgical microscope system according to claim 2, wherein at least one of the two displays is a rigid organic light-emitting diode (OLED) display.

4. The surgical microscope system according to claim 2, wherein at least one of the two displays is a flexible organic light-emitting diode (OLED) display.

5. The surgical microscope system according to claim 2, wherein the OLED display is arranged on the microscope body and the microscope body houses a displaceable splitter prism whereby an overlay beam path from the OLED display can be selectably coupled into a microscope beam path by the splitter prism.

6. The surgical microscope system according to claim 1, wherein the two displays present video images and technical data and a position symbol corresponding to a current X-Y position of the microscope body.

7. A surgical microscope system comprising:
a stand having a carrier arm;
a microscope body having an eyepiece tube;
an X-Y coupling for mounting the microscope body on the carrier arm;
two displays arranged each at a different attachment location selected from a group of attachment locations consisting of: on an exterior of the microscope body, on the X-Y coupling, on the carrier arm, and on the eyepiece tube, each display being arranged in the immediate field of view of a viewer's eye; and
a control system operable to display identical data on both of the two displays or different data on the two displays;
wherein at least one of the two displays is an organic light-emitting diode (OLED) display, wherein the OLED display is arranged on the microscope body and the microscope body houses a displaceable splitter prism whereby an overlay beam path from the OLED display can be selectably coupled into a microscope beam path by the splitter prism, and the OLED display is a display emitting on both sides thereof, such that one side can be overlaid into the microscope beam path and the other side can be viewed by a viewer.

\* \* \* \* \*